US010489788B1

(12) United States Patent
Edwards et al.

(10) Patent No.: US 10,489,788 B1
(45) Date of Patent: Nov. 26, 2019

(54) DETERMINING A BODY MASS INDEX OF A USER OF A TRANSACTION DEVICE AND VERIFYING THE USER FOR UTILIZATION OF THE TRANSACTION DEVICE BASED ON THE BODY MASS INDEX

(71) Applicant: Capital One Services, LLC, McLean, VA (US)

(72) Inventors: Joshua Edwards, Philadelphia, PA (US); Abdelkadar M'Hamed Benkreira, Washington, DC (US); Michael Mossoba, Arlington, VA (US)

(73) Assignee: Capital One Services, LLC, McLean, VA (US)

( * ) Notice: Subject to any disclaimer, the term of this patent is extended or adjusted under 35 U.S.C. 154(b) by 0 days.

(21) Appl. No.: 16/362,100

(22) Filed: Mar. 22, 2019

(51) Int. Cl.
| | |
|---|---|
| *G06Q 20/20* | (2012.01) |
| *G06Q 20/40* | (2012.01) |
| *G06N 20/00* | (2019.01) |
| *G01G 19/44* | (2006.01) |
| *A61B 5/00* | (2006.01) |
| *A61B 5/1171* | (2016.01) |
| *G06Q 20/10* | (2012.01) |

(Continued)

(52) U.S. Cl.
CPC .......... *G06Q 20/405* (2013.01); *A61B 5/1171* (2016.02); *A61B 5/4872* (2013.01); *A61B 5/7264* (2013.01); *G01G 19/44* (2013.01); *G06N 20/00* (2019.01); *A61B 2576/00* (2013.01); *G06N 3/04* (2013.01); *G06N 20/10* (2019.01); *G06Q 20/1085* (2013.01); *G06Q 20/20* (2013.01)

(58) Field of Classification Search
CPC .............................. G06Q 40/00; G06Q 20/405
See application file for complete search history.

(56) References Cited

U.S. PATENT DOCUMENTS

| | | | | |
|---|---|---|---|---|
| 3,970,992 A | * | 7/1976 | Boothroyd | G06Q 40/02 705/43 |
| 2002/0013895 A1 | * | 1/2002 | Kelley | G06Q 30/0621 713/1 |

(Continued)

OTHER PUBLICATIONS

Enes Kocabey, Mustafa Camurcu, Ferda Ofli, Yusuf Aytar, Javier Marin, Antonio Torralba, and Ingmar Weber, Face-to-BMI: Using Computer Vision to Infer Body Mass Index on Social Media, 2017, Association for the Advancement of Artificial Intelligence, web, 572-575 (Year: 2017).*

*Primary Examiner* — I Jung Liu
(74) *Attorney, Agent, or Firm* — Harrity & Harrity, LLP

(57) ABSTRACT

A device receives sensor data that provides an indication of a height of a user of a transaction device, receives camera data that includes one or more images of the user, and scale data that provides an indication of a weight of the user. The device identifies one or more features associated with the user based on the camera data and processes the sensor data, the scale data, and feature information describing the one or more features, with a machine learning model, to estimate a body mass index of the user. The device determines whether the user is verified for utilizing the transaction device to conduct a transaction based on the body mass index and one or more credentials associated with the user and performs one or more actions based on determining whether the user is verified for utilizing the transaction device to conduct the transaction.

20 Claims, 12 Drawing Sheets

(51) Int. Cl.
*G06N 20/10* (2019.01)
*G06N 3/04* (2006.01)

(56) References Cited

U.S. PATENT DOCUMENTS

| | | |
|---|---|---|
| 2012/0022348 A1 | 1/2012 | Droitcour et al. |
| 2014/0247155 A1 | 9/2014 | Proud |
| 2015/0177053 A1 | 6/2015 | Bagan |
| 2017/0143282 A1 | 5/2017 | Kovacs et al. |

\* cited by examiner

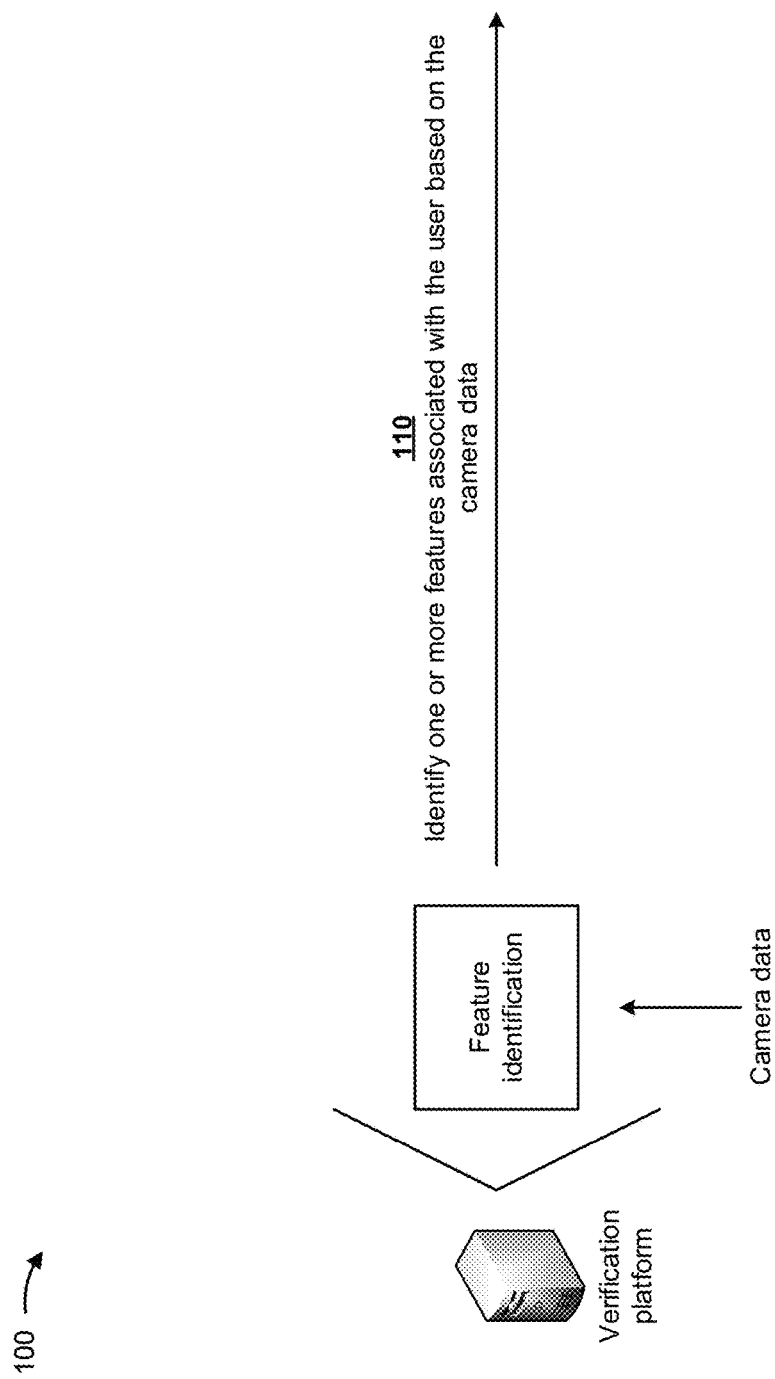

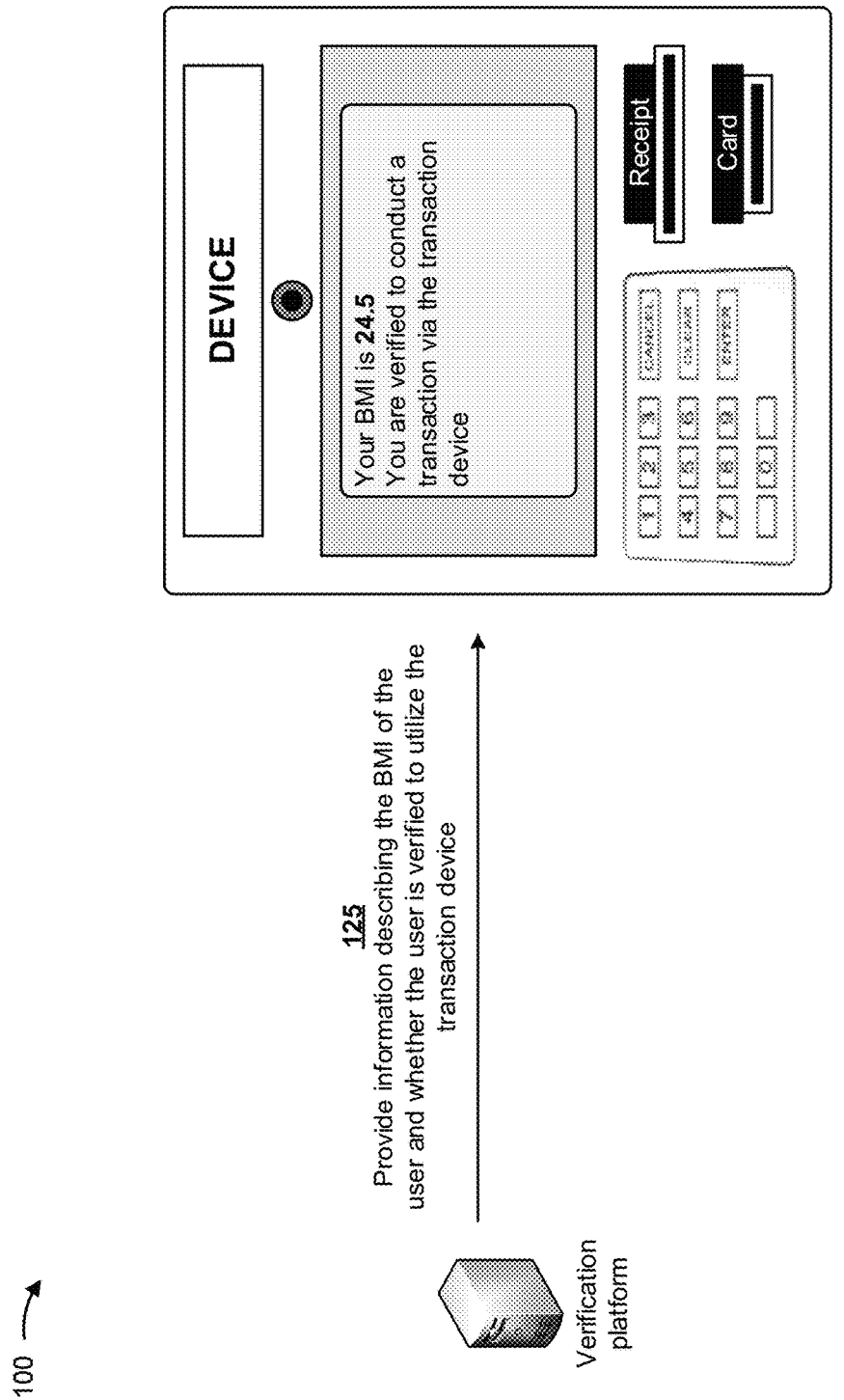

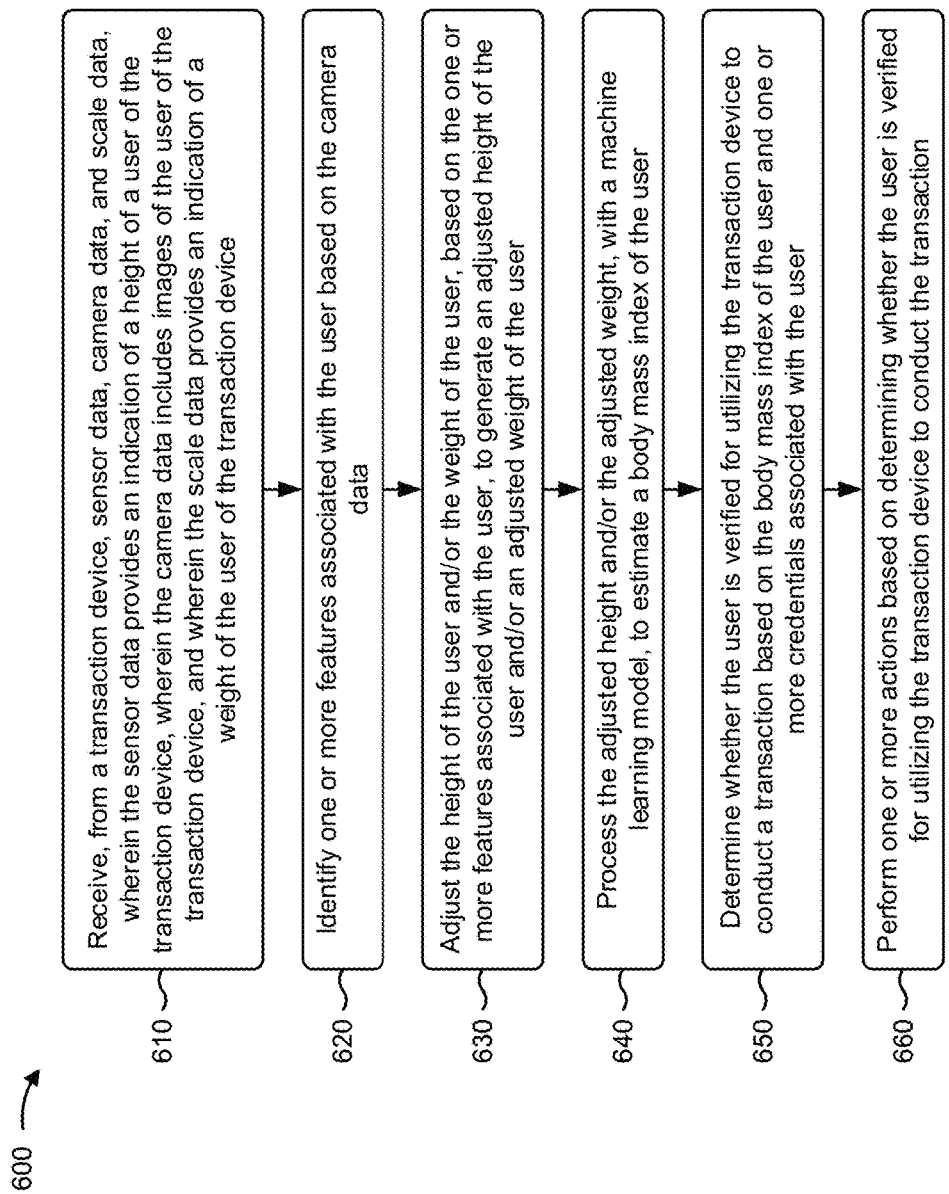

DETERMINING A BODY MASS INDEX OF A USER OF A TRANSACTION DEVICE AND VERIFYING THE USER FOR UTILIZATION OF THE TRANSACTION DEVICE BASED ON THE BODY MASS INDEX

BACKGROUND

A transaction device may include an automated teller machine (ATM) device, a point of sale (POS) device, a kiosk device, and/or the like. A user of a transaction device may provide a credential associated with an account of the user (e.g., a personal identification number (PIN), an account number, a telephone number, and/or the like) in order to conduct a transaction via the transaction device.

SUMMARY

According to some implementations, a method may include receiving, from a sensor associated with a transaction device, sensor data, wherein the sensor data may provide an indication of a height of a user of the transaction device. The method may include receiving, from a camera associated with the transaction device, camera data, wherein the camera data may include one or more images of the user of the transaction device and receiving, from a scale associated with the transaction device, scale data, wherein the scale data may provide an indication of a weight of the user of the transaction device. The method may include identifying one or more features associated with the user, based on the camera data, and processing the sensor data, the scale data, and feature information describing the one or more features, with a machine learning model, to estimate a body mass index of the user. The method may include determining whether the user is verified for utilizing the transaction device to conduct a transaction based on the body mass index of the user and one or more credentials associated with the user, and performing one or more actions based on determining whether the user is verified for utilizing the transaction device to conduct the transaction.

According to some implementations, a device may include one or more memories and one or more processors communicatively coupled to the one or more memories, configured to receive, from a transaction device, one or more credentials associated with a user of a transaction device and receive sensor data, camera data, and scale data from the transaction device, wherein the sensor data may provide an indication of a height of the user of the transaction device, wherein the camera data may include images of the user of the transaction device, and wherein the scale data may provide an indication of a weight of the user of the transaction device. The one or more processors may identify one or more features associated with the user based on the camera data and may process the sensor data, the scale data, and feature information describing the one or more features, with a machine learning model, to estimate a body mass index of the user. The one or more processors may compare the body mass index of the user and the one or more credentials associated with the user with information associated with an account associated with the user and may determine whether the user is verified for utilizing the transaction device to conduct a transaction, based on comparing the body mass index and the one or more credentials with the information associated with the account. The one or more processors may perform one or more actions based on determining whether the user is verified for utilizing the transaction device to conduct the transaction.

According to some implementations, a non-transitory computer-readable medium may store instructions that include one or more instructions that, when executed by one or more processors of a device, cause the one or more processors to receive, from a transaction device, sensor data, camera data, and scale data, wherein the sensor data may provide an indication of a height of a user of the transaction device, wherein the camera data may include images of the user of the transaction device, and wherein the scale data may provide an indication of a weight of the user of the transaction device. The one or more instructions may cause the one or more processors to identify one or more features associated with the user, based on the camera data, and adjust the height of the user and/or the weight of the user, based on the one or more features associated with the user, to generate an adjusted height of the user and/or an adjusted weight of the user. The one or more instructions may cause the one or more processors to process the adjusted height and/or the adjusted weight, with a machine learning model, to estimate a body mass index of the user and determine whether the user is verified for utilizing the transaction device to conduct a transaction, based on the body mass index of the user and one or more credentials associated with the user. The one or more instructions may cause the one or more processors to perform one or more actions based on determining whether the user is verified for utilizing the transaction device to conduct the transaction.

BRIEF DESCRIPTION OF THE DRAWINGS

FIGS. 1A-1G are diagrams of an example implementation described herein.

FIGS. 4-6 are flow charts of example processes for determining a body mass index of a user of a transaction device and verifying the user for utilization of the transaction device based on the body mass index.

DETAILED DESCRIPTION

The following detailed description of example implementations refers to the accompanying drawings. The same reference numbers in different drawings may identify the same or similar elements.

In order to provide more security for a transaction, a transaction device may require a user to provide additional credentials in order to conduct the transaction via the transaction device. For example, the transaction device may require the user to input a security code, password, and/or the like provided to a mobile device associated with the user. However, providing such additional credentials creates a technical problem of requiring the user to have the mobile device present to receive the security code, password, and/or the like.

Some implementations described herein provide a verification platform that determines a body mass index of a user of a transaction device and verifies the user for utilization of the transaction device based on the body mass index. For example, the verification platform may receive, from a sensor associated with a transaction device, sensor data, wherein the sensor data may provide an indication of a height of a user of the transaction device. The verification platform may receive, from a camera associated with the transaction device, camera data, wherein the camera data may include images of the user of the transaction device, and may receive, from a scale associated with the transaction device, scale data, wherein the scale data may provide an indication of a weight of the user of the transaction device. The verification platform may identify one or more features associated with the user based on the camera data and may process the sensor data, the scale data, and feature information describing the one or more features, with a machine learning model, to estimate a body mass index of the user. The verification platform may determine whether the user is verified for utilizing the transaction device to conduct a transaction based on the body mass index of the user and one or more credentials (e.g., a personal identifier, an account number, the height of the user, the weight of the user, and/or the like) associated with the user and may perform one or more actions based on determining whether the user is verified for utilizing the transaction device to conduct the transaction.

In this way, the verification platform provides more security for a transaction without requiring additional action from a user, which conserves resources (e.g., processing resources, memory resources, and/or the like) that would otherwise be wasted in providing and processing additional credentials of the user. The verification platform also provides users with a simple mechanism to track their health while performing activities that they already perform (e.g., utilizing a transaction device).

Figure 1A:
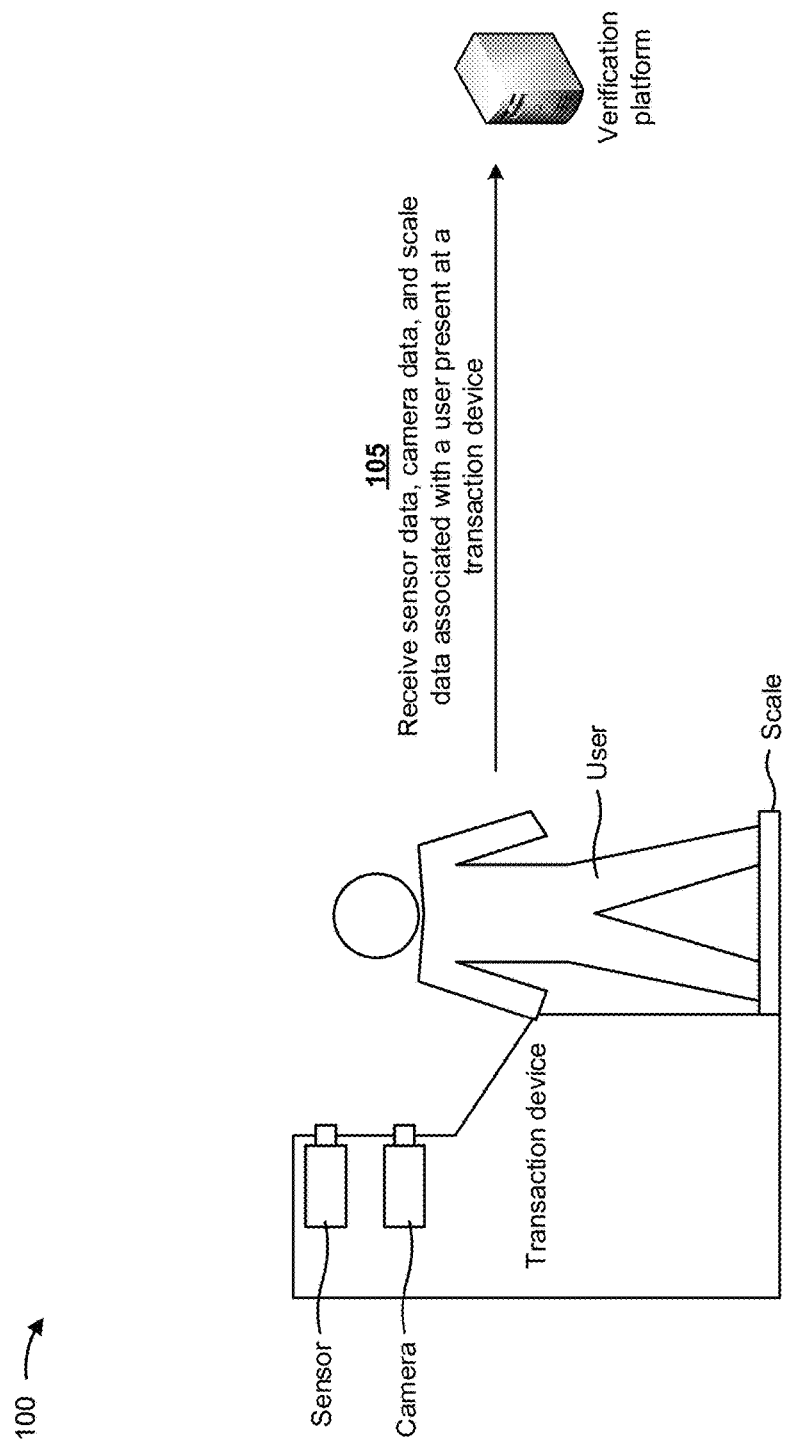

FIGS. 1A-1G are diagrams of an example implementation 100 described herein. As shown in FIG. 1A, a transaction device may be associated with a user and a verification platform. The user of the transaction device may utilize the transaction device to conduct a transaction (e.g., deposit money, receive money, check account balances, and/or the) with the verification platform. As further shown, the transaction device may include a sensor for measuring a height of the user, a camera for identifying features associated with the user, and a scale for measuring a weight of the user, as the user conducts the transaction.

As further shown in FIG. 1A, and by reference number 105, the verification platform may receive sensor data, camera data, and scale data associated with the user present at the transaction device. In some implementations, the sensor data may be generated by the sensor and may include data that provides an indication of a height of the user. In some implementations, the sensor may provide the sensor data to the verification platform and/or to the transaction device (e.g., which provides the sensor data to the verification platform). In some implementations, the camera data may be generated by the camera and may include images of the user of the transaction device. In some implementations, the camera may provide the camera data to the verification platform and/or to the transaction device (e.g., which provides the camera data to the verification platform). In some implementations, the scale data may be generated by the scale and may include data that provides an indication of a weight of the user. In some implementations, the scale may provide the scale data to the verification platform and/or to the transaction device (e.g., which provides the scale data to the verification platform).

Figure 1B:
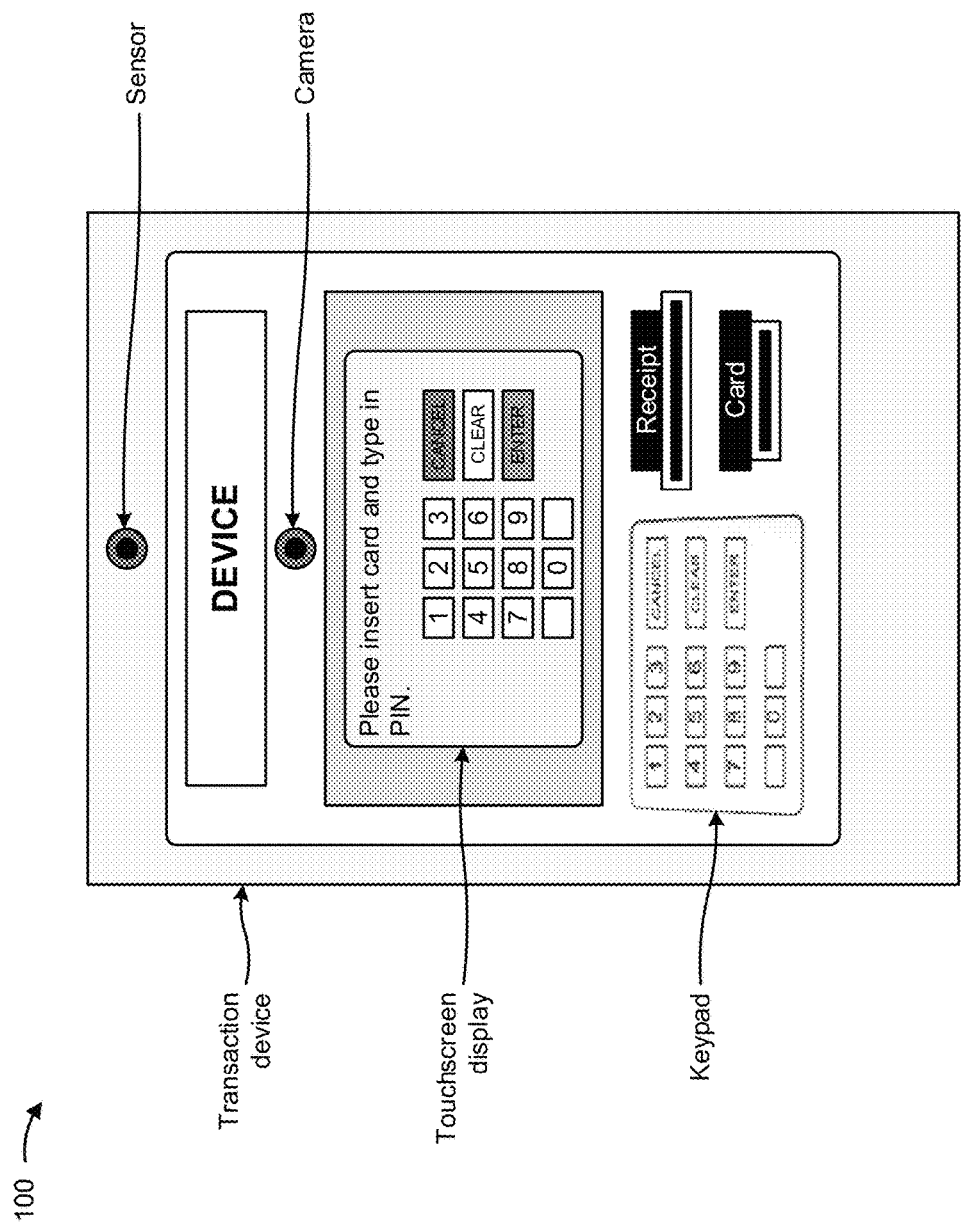

As shown in FIG. 1B, the transaction device may include a touchscreen display, a keypad, the camera, the sensor, and/or the like. In some implementations, the transaction device may include a display device and keypad, a touchscreen display and no keypad, and/or one or more other components (e.g., a printer for printing a receipt, a slot for receiving a transaction card, and/or the like). In some implementations, the touchscreen device may enable the user to input sensitive information (e.g., a PIN, a user identifier, and/or the like), view sensitive information (e.g., an account number, an account balance, an image of a keypad, and/or the like), and/or the like. In one example, the user may utilize the image of the keypad to input a PIN of the user, to input an amount of money to withdraw, to select an account from which to withdraw the money, and/or the like.

In some implementations, the keypad may include keys, with particular numbers (e.g., 0 through 9), that may be used to enter a PIN of the user, an enter key that may be used to enter or input the PIN provided by the user, a clear key that may be used to clear the PIN input by the user, a cancel key that may be used to cancel a transaction, and/or the like. In some implementations, information input via the keypad may be displayed via the touchscreen display or a display device.

In some implementations, the camera may include an image capture device (e.g., a digital camera) that may be used to capture an image of the user and surroundings of the user, a video capture device (e.g., a video camera) that may be used to capture a video of the user and the surroundings of the user, and/or the like.

In some implementations, the sensor may include an optical sensor (e.g., an infrared sensor, a photoconductive sensor, a photovoltaic sensor, a photodiode, a phototransistor, and/or the like) that may be used to measure an intensity of light for the surroundings of the user. In some implementations, the sensor may be used to determine position information indicating one or more positions of the user of the transaction device (e.g., a height of the user relative to the transaction device, a distance the user is standing from the transaction device, and/or the like) and/or the surroundings of the user (e.g., a position of a person behind the user, relative to the transaction device). In some implementations, the sensor may be used to determine lighting information indicating lighting conditions around the transaction device, the user, and/or the surroundings of the user.

As shown in FIG. 1C, and by reference number 110, the verification platform may identify one or more features associated with the user based on the camera data. In some implementations, the one or more features associated with the user may include features indicating a width of the user, whether the user is holding an item (e.g., a bag, a child, a backpack, and/or the like), a type of item being held by the user, whether the user is wearing a hat, a type of hat worn by the user, a type of shoes worn by the user, whether the user is wearing a jacket, a type of jacket worn by the user, and/or the like.

In some implementations, the verification platform may utilize a variety of image classifiers to determine if the camera data contains an object of interest (e.g., one or more features). For example, the verification platform may utilize one or more of a histogram of oriented gradients (HOG) classifier, a support vector machines (SVM) classifier, a Haar cascade classifier, a convolution neural network (CNN) classifier, and/or the like, to identify the one or more features in the camera data. The HOG classifier is used in computer vision and image processing for the purpose of object detection and counts occurrences of gradient orientation in localized portions of an image. The SVM classifier is a discriminative classifier formally defined by a separating hyperplane that separates classes. In other words, given labeled training data (e.g., supervised learning), the SVM classifier outputs an optimal hyperplane which categorizes different classes. The Haar cascade classifier is a machine learning based approach where a cascade function is trained from several positive and negative images and is used to detect objects in other images. The CNN classifier is a technique that utilizes fewer parameters, which greatly improves a time taken to learn and reduces an amount of data required to train the classifier. Instead of a fully connected network of weights from each pixel of an image, the CNN classifier utilizes enough weights to look at a small portion of the image.

Figure 1D:
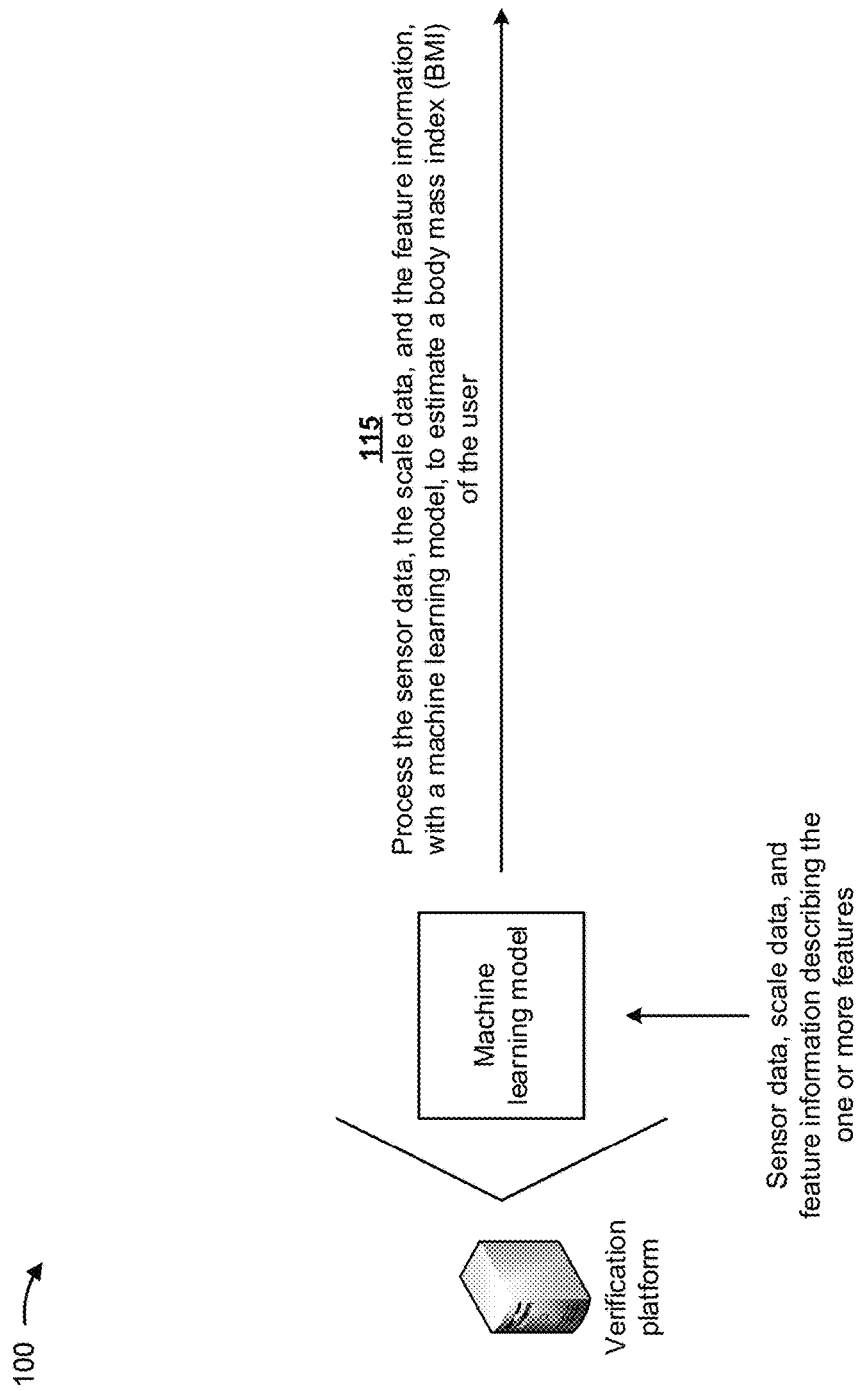

As shown in FIG. 1D, and by reference number 115, the verification platform may process the sensor data, the scale data, and feature information describing the one or more features associated with the user, with a machine learning model, to estimate a body mass index (BMI) of the user. In some implementations, the machine learning model may include a pattern recognition model that generates different BMIs for different users based on sensor data, scale data, feature information, and/or the like. In some implementations, the verification platform may perform a training operation on the machine learning model, with historical data to train the model to determine BMI for individuals based on heights and weights of users identified in the historical data. The historical data may include historical sensor data received from sensors, historical scale data received from scales, historical feature information describing one or more features associated with users of transaction devices, calculated BMIs of the user, actual BMIs of the users, and/or the like.

The verification platform may separate the historical data into a training set, a validation set, a test set, and/or the like. The training set may be utilized to train the machine learning model. The validation set may be utilized to validate results of the trained machine learning model. The test set may be utilized to test operations of the machine learning model. In some implementations, the verification platform may train the machine learning model using, for example, an unsupervised training procedure and based on the historical data. For example, the verification platform may perform dimensionality reduction to reduce the historical data to a minimum feature set, thereby reducing resources (e.g., processing resources, memory resources, and/or the like) needed to train the machine learning model, and may apply a classification technique to the minimum feature set.

In some implementations, the verification platform may use a logistic regression classification technique to determine a categorical outcome (e.g., that the historical height and weight information is associated with particular BMIs of users). Additionally, or alternatively, the verification platform may use a naïve Bayesian classifier technique. In this case, the verification platform may perform binary recursive partitioning to split the historical data into partitions and/or branches and use the partitions and/or branches to perform predictions (e.g., that the historical data indicates BMIs of users). Based on using recursive partitioning, the verification platform may reduce utilization of computing resources relative to manual, linear sorting and analysis of data points, thereby enabling use of thousands, millions, or billions of data points to train the machine learning model, which may result in a more accurate model than using fewer data points.

Additionally, or alternatively, the verification platform may use a support vector machine (SVM) classifier technique to generate a non-linear boundary between data points in the training set. In this case, the non-linear boundary is used to classify test data into a particular class.

Additionally, or alternatively, the verification platform may train the machine learning model using a supervised training procedure that includes receiving input to the machine learning model from a subject matter expert, which may reduce an amount of time, an amount of processing resources, and/or the like to train the machine learning model relative to an unsupervised training procedure. In some implementations, the verification platform may use one or more other model training techniques, such as a neural network technique, a latent semantic indexing technique, and/or the like. For example, the verification platform may perform an artificial neural network processing technique (e.g., using a two-layer feedforward neural network architecture, a three-layer feedforward neural network architecture, and/or the like) to perform pattern recognition with regard to patterns of the historical data. In this case, using the artificial neural network processing technique may improve an accuracy of the trained machine learning model generated by the verification platform by being more robust to noisy, imprecise, or incomplete data, and by enabling the verification platform to detect patterns and/or trends undetectable to human analysts or systems using less complex techniques.

In some implementations, the verification platform may receive the machine learning model from another source. In such implementations, the machine learning model may be trained as described above.

In some implementations, the machine learning model may factor in the feature information before determining the BMI of the user, since the feature information (e.g., holding a baby, wearing a big coat, wearing heavy shoes or shoes with tall heels, etc.) may affect the height and/or the weight of the user, and thus, the determined BMI. For example, the feature information may include information indicating clothing that the user is wearing, and the machine learning model may account for the clothing when calculating the BMI (e.g., by adjusting the height and/or the weight of the user). In some implementations, the verification platform may determine a width of the user (e.g., based on the camera data) and may utilize the width to determine clothing worn by the user and to estimate a weight of the clothing. In some implementations, weather may be a factor that affects clothing worn by the user and the estimate of the BMI, and the verification platform may utilize the weather to estimate the BMI. In some implementations, the verification platform may cause the transaction device to request that the user provide an estimated weight of clothes worn by the user, an estimated weight of the user, an actual height of the user, and/or the like; empty pockets if carrying a lot; remove a hat; and/or the like.

In some implementations, the verification platform may determine a baseline BMI for the user, after the BMI is calculated for the user a particular quantity of times, and may associate the baseline BMI with the user profile. In some implementations, the user may confirm the BMI determined by the verification platform, and the verification platform may associate the confirmed BMI with the user profile.

Figure 1E:
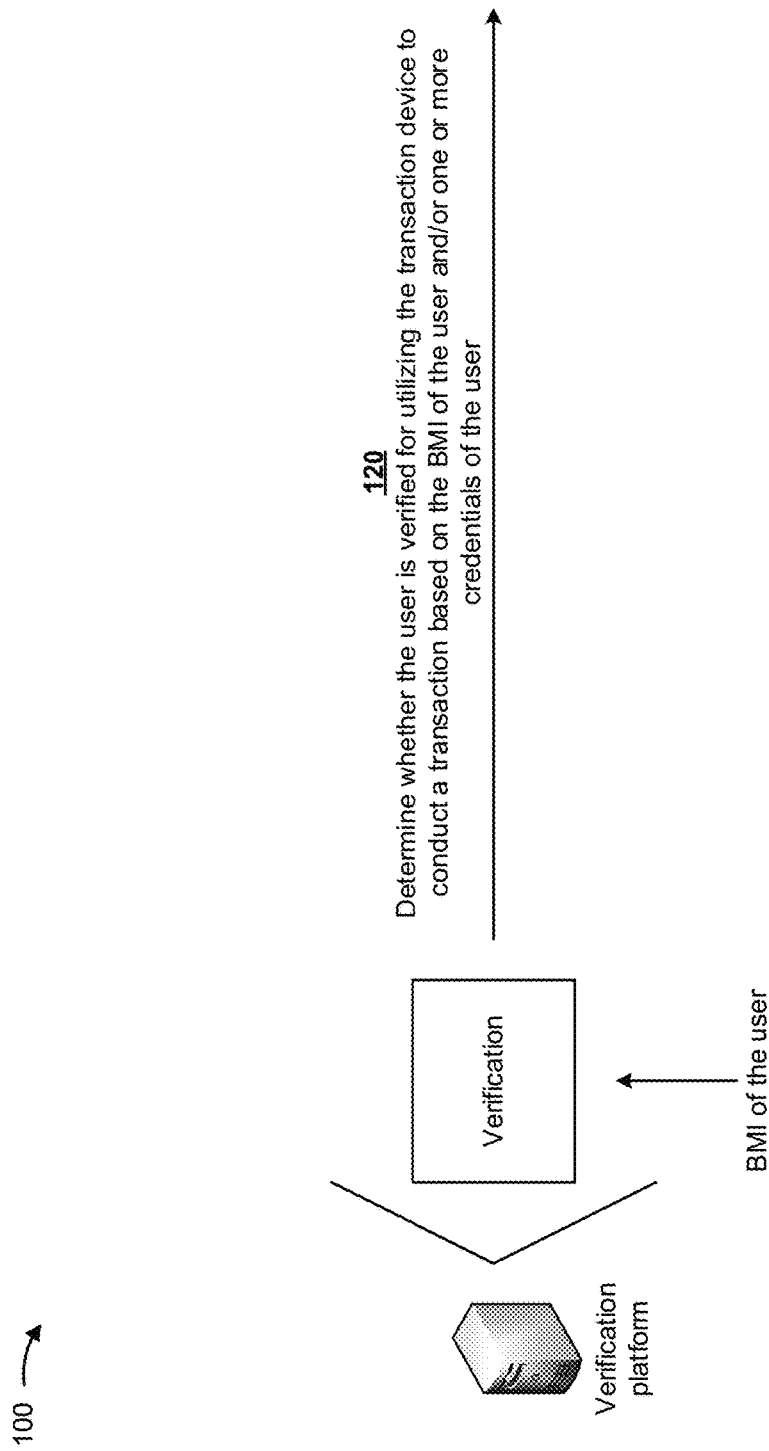

As shown in FIG. 1E, and by reference number 120, the verification platform may determine whether the user is verified for utilizing the transaction device to conduct a transaction based on the BMI of the user and/or one or more credentials of the user. In some implementations, the one or more credentials of the user may include the height of the user, the weight of the user, a personal identification number (PIN) associated with the user, an account number associated with the user, a telephone number associated with the user, and/or the like, associated with a user profile (e.g., a user record) of the user. In some implementations, the verification platform may verify the user for utilizing the transaction device to conduct a transaction when the BMI of the user matches or substantially matches a BMI associated with the user profile, and the one or more credentials matches or substantially matches one of the height of the user, the weight of the user, the PIN associated with the user, the account number associated with the user, the telephone number associated with the user, and/or the like. In some implementations, the verification platform may accord more weight to the BMI than to the one or more credentials when the user regularly utilizes transaction devices and has the BMI determined.

In some implementations, the verification platform may not verify the user for utilizing the transaction device to conduct a transaction when the BMI of the user does not match and/or does not substantially match the BMI associated with the user profile, or the one or more credentials do not match or does not substantially match one of the height of the user, the weight of the user, the PIN associated with the user, the account number associated with the user, the telephone number associated with the user, and/or the like. In such implementations, the verification platform may request another verification factor (e.g., another credential of the user); request remeasurement of the BMI; request different verification factors depending on the amount by which the BMI does not match (e.g., if the BMI is substantially different than the BMI associated with the user profile (e.g., within five percent, ten percent, and/or the like), the verification platform may request two additional verification factors, may signal an alert, may decline the transaction, may limit an amount of money withdrawn by the user, may prevent money from being withdrawn by the user, etc.); and/or the like.

As shown in FIG. 1F, and by reference number 125, the verification platform may provide information describing the BMI of the user and whether the user is verified to utilize the transaction device. In some implementations, the verification platform may provide the information describing the BMI of the user and whether the user is verified to utilize the transaction device, as a user interface, to the transaction device. The transaction device may receive the user interface and may display the user interface to the user (e.g., via the touchscreen display). As further shown in FIG. 1F, the user interface may include information indicating that the BMI of the user is 24.5 and that the user is verified to conduct a transaction via the transaction device.

Figure 1G:
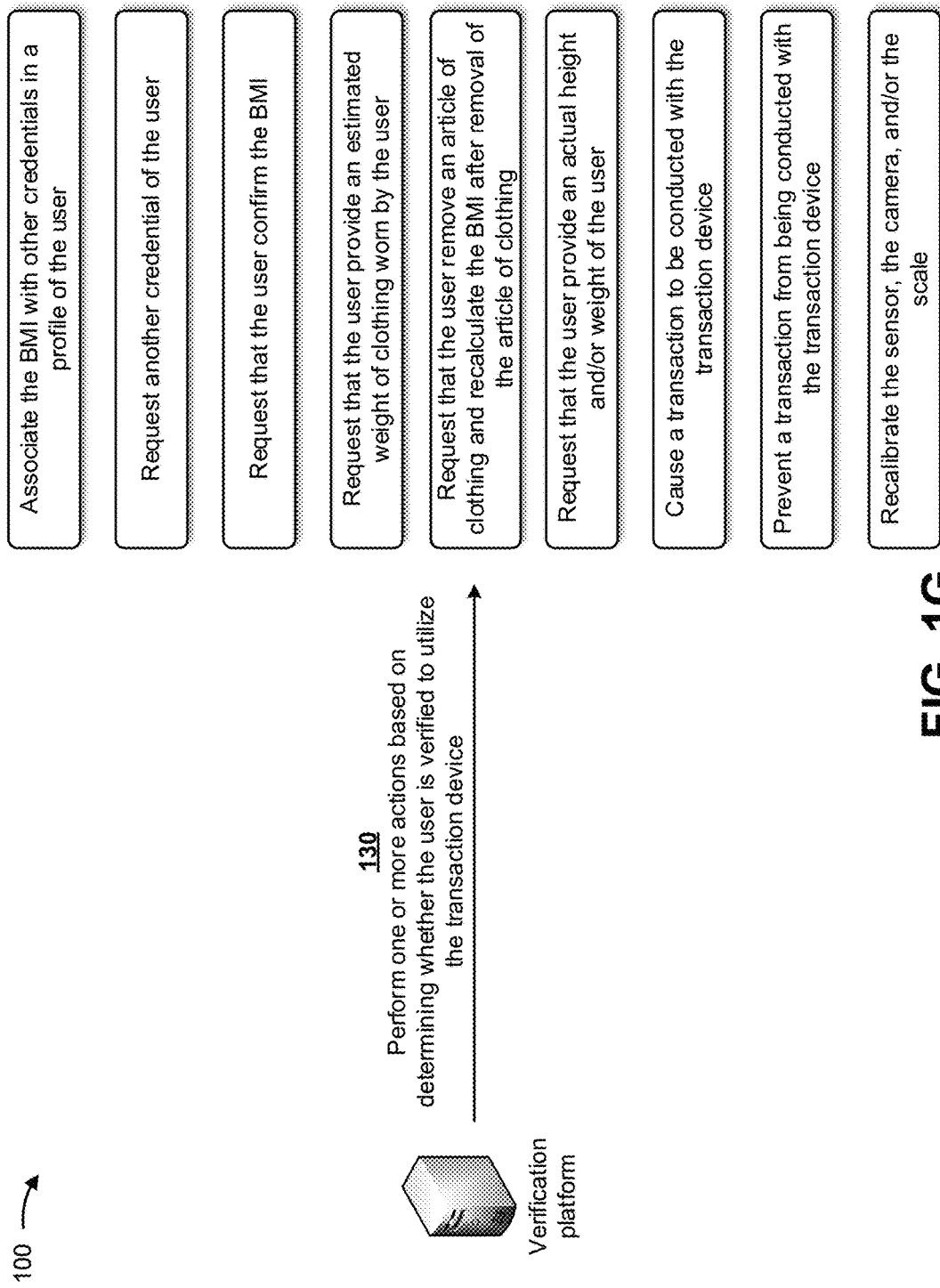

As shown in FIG. 1G, and by reference number 130, the verification platform may perform one or more actions based on determining whether the user is verified to utilize the transaction device. For example, the one or more actions may include the verification platform associating the BMI with other credentials in a profile (e.g., the user profile) of the user. In this way, the verification platform utilizes the BMI as an additional credential for verifying the user, which provides an additional layer of security.

In some implementations, the one or more actions may include the verification platform causing the transaction device to request another credential from the user. In this way, the verification platform requests additional credentials when the BMI does not match a BMI associated with the user profile, which provides additional security for the transaction device.

In some implementations, the one or more actions may include the verification platform causing the transaction device to request that the user confirm the BMI. In this way, the verification platform verifies outputs of the machine learning model, which improves model performance in the future.

In some implementations, the one or more actions may include the verification platform causing the transaction device to request that the user provide an estimated weight of clothing worn by the user. In this way, the verification platform can factor in the weight of the clothing before calculating the BMI of the user, which prevents erroneous BMI calculations.

In some implementations, the one or more actions may include the verification platform causing the transaction device to request that the user remove an article of clothing, and recalculating the BMI after removal of the article of clothing. In this way, the verification platform can take into account the weight of the clothing before recalculating the BMI of the user, which prevents erroneous BMI calculations.

In some implementations, the one or more actions may include the verification platform causing the transaction device to request that the user provide an actual height and/or weight of the user. In this way, the verification platform verifies outputs of the machine learning model, which improves model performance in the future. Furthermore, the verification platform verifies that the sensor and the scale are functioning correctly and do not need to be recalibrated and/or repaired.

In some implementations, the one or more actions may include the verification platform causing the transaction to be conducted with the transaction device. In this way, the verification platform provides a non-invasive mechanism to verify the user for transactions and improves the user experience.

In some implementations, the one or more actions may include the verification platform preventing the transaction from being conducted with the transaction device. In this way, the prevention platform provides another layer of security for authenticating users of transaction devices.

In some implementations, the one or more actions may include the verification platform being configured to cause the sensor, the camera, and/or the scale to be recalibrated and/or repaired. For example, the verification platform may dispatch a technician or a robot to recalibrate and/or repair the sensor, the camera, and/or the scale. In this way, the verification platform ensures that the sensor, the camera, and/or the scale are performing correctly and providing accurate information.

In some implementations, the one or more actions may include the verification platform causing the transaction device to request that the user put down an object that the user is holding and determining a weight of the object. In this way, the verification platform may utilize the weight of an object, when the user or other users are holding the object, to accurately determine the weight and the BMI of the user or the other users.

In this way, several different stages of the process for determining a body mass index of a user of a transaction device and verifying the user for utilization of the transaction device based on the body mass index are automated based on machine learning, which may remove human subjectivity and waste from the process, and which may improve speed and efficiency of the process and conserve computing resources (e.g., processing resources, memory resources, and/or the like). Furthermore, implementations described herein use a rigorous, computerized process to perform tasks or roles that were not previously performed or were previously performed using subjective human intuition or input. For example, currently there does not exist a technique that determines a body mass index of a user of a transaction device and verifies the user for utilization of the transaction device based on the body mass index. Finally, automating the process for determining a body mass index of a user of a transaction device and verifying the user for utilization of the transaction device based on the body mass index conserves computing resources (e.g., processing resources, memory resources, and/or the like) that would otherwise be wasted in attempting to verify the user for utilization of the transaction device.

As indicated above, FIGS. 1A-1G are provided merely as examples. Other examples may differ from what is described with regard to FIGS. 1A-1G.

Figure 2:
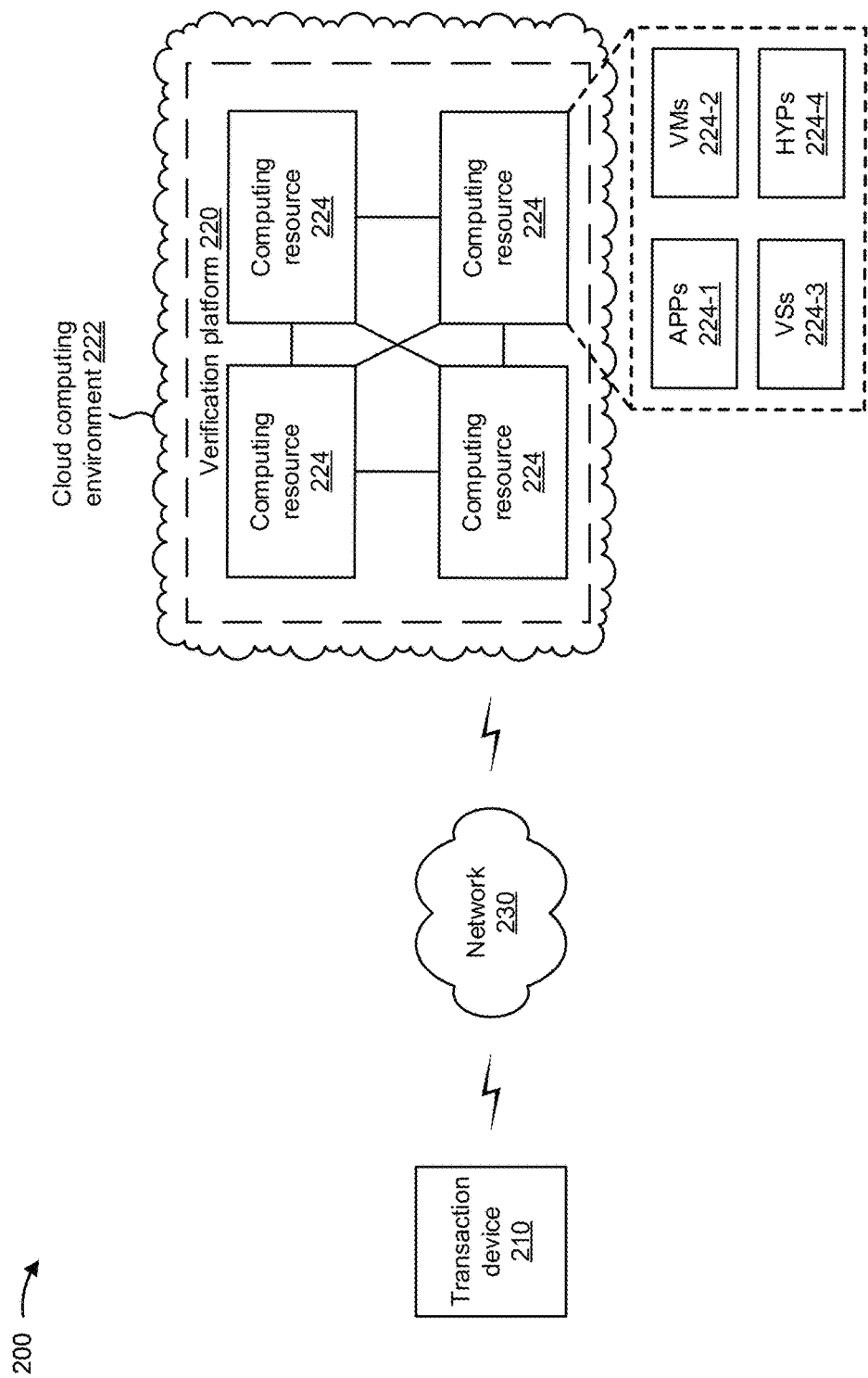
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a transaction device 210, a verification platform 220, and a network 230. Devices of environment 200 may interconnect via wired connections, wireless connections, or a combination of wired and wireless connections.

Transaction device 210 includes one or more devices capable of receiving, generating, storing, processing, and/or providing information, such as information described herein. For example, transaction device 210 may include an automated teller machine (ATM) device, a point of sale (POS) device, a kiosk device, and/or the like.

The ATM device may include an electronic telecommunications device that enables customers of financial institutions to perform financial transactions, such as cash withdrawals, deposits, transferring funds, obtaining account information, and/or the like, at any time and without direct interaction with employees of the financial institutions. The POS device may include an electronic device used to process transaction card payments at retail locations. The POS device may read information from a transaction card (e.g., a credit card, a debit card, a gift card, and/or the like), and may determine whether there are sufficient funds in an account associated with the transaction card for a transaction. The POS device may transfer funds from the account associated with the transaction card to an account of a retailer and may record the transaction. The kiosk device may include a computer terminal featuring specialized hardware and/or software that provides access to information and/or applications for communication, commerce, entertainment, education, and/or the like.

In some implementations, transaction device 210 may include an input element (e.g., a keypad, a keyboard, a touchscreen display, and/or the like) for receiving input data from a user of the transaction device, a sensor for determining a height associated with the user, a camera for determining features associated with the user, a scale for determining a weight associated with the user, and/or the like.

The sensor may include a laser sensor to measure the height of the user, an ultrasound sensor to measure the height of the user, a camera (e.g., with a reference point, such as a ruler, a background object, and/or the like) to measure the height of the user, and/or the like. In some implementations, the sensor may receive information from and/or transmit information to transaction device 210 and/or verification platform 220.

The camera may include an image and/or video capturing device, a three-hundred and sixty-degree camera, a digital camera, or a similar type of device. In some implementations, the camera may receive information from and/or transmit information to transaction device 210 and/or verification platform 220.

The scale may include a device to measure weight or mass, such as a mass scale, a weight scale, a mass balance, a weight balance, or a similar type of device. In some implementations, the scale may receive information from and/or transmit information to transaction device 210 and/or verification platform 220.

Verification platform 220 includes one or more devices that determine a body mass index of a user of a transaction device and verify the user for utilization of the transaction device based on the body mass index. In some implementations, verification platform 220 may be designed to be modular such that certain software components may be swapped in or out depending on a particular need. As such, verification platform 220 may be easily and/or quickly reconfigured for different uses. In some implementations, verification platform 220 may receive information from and/or transmit information to one or more transaction devices 210.

In some implementations, as shown, verification platform 220 may be hosted in a cloud computing environment 222. Notably, while implementations shown and described herein describe verification platform 220 as being hosted in cloud computing environment 222, in some implementations, verification platform 220 may be non-cloud-based (i.e., may be implemented outside of a cloud computing environment) or may be partially cloud-based.

Cloud computing environment 222 includes an environment that hosts verification platform 220. Cloud computing environment 222 may provide computation, software, data access, storage, etc. services that do not require end-user knowledge of a physical location and configuration of system(s) and/or device(s) that host verification platform 220. As shown, cloud computing environment 222 may include a group of computing resources 224 (referred to collectively as "computing resources 224" and individually as "computing resource 224").

Computing resource 224 includes one or more personal computers, workstation computers, server devices, and/or other types of computation and/or communication devices. In some implementations, computing resource 224 may host verification platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by transaction device 210. Application 224-1 may eliminate a need to install and execute the software applications on transaction device 210. For example, application 224-1 may include software associated with verification platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program and may support a single process. In some implementations, virtual machine 224-2 may execute on behalf of a user (e.g., a user of transaction device 210 or an operator of verification platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
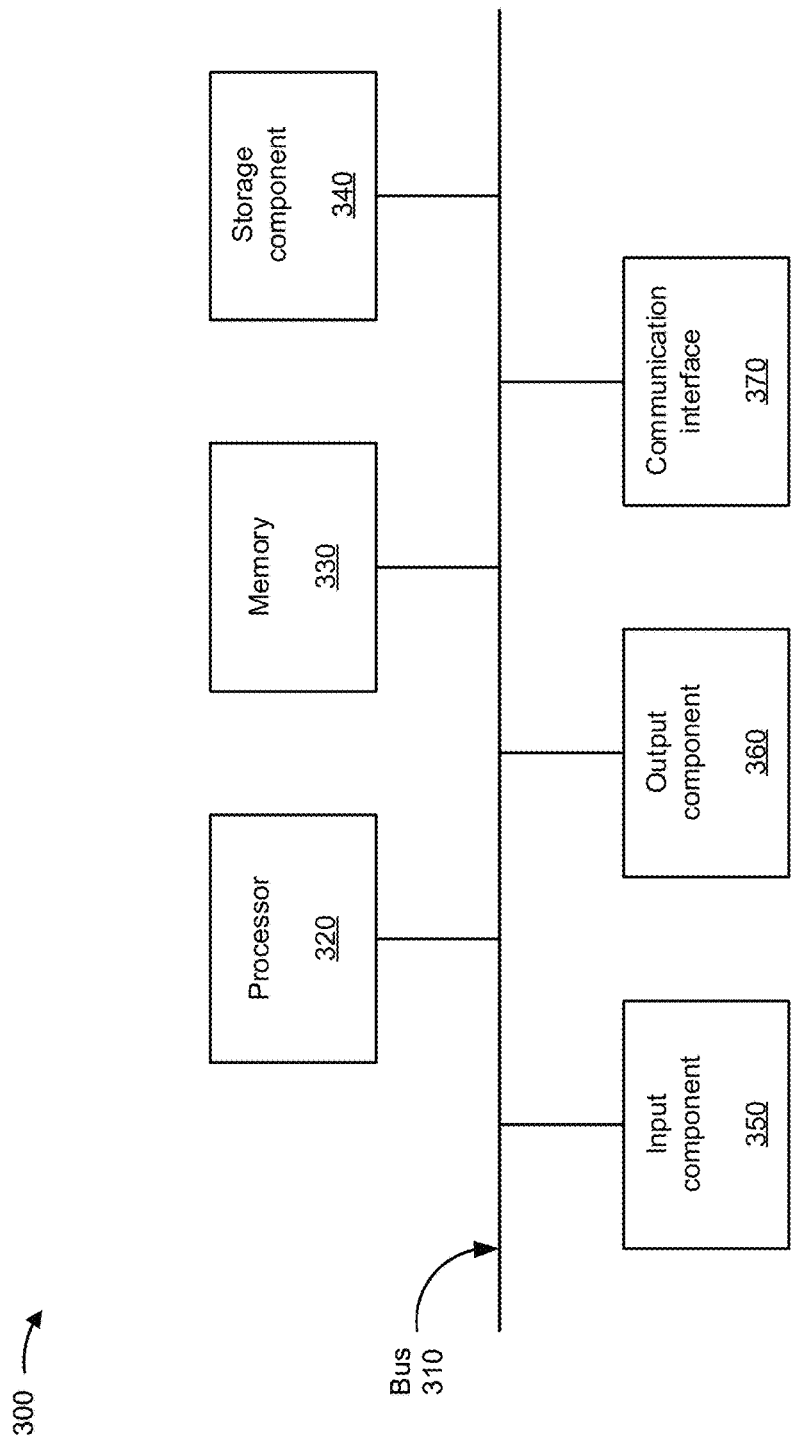
FIG. 3 is a diagram of example components of one or more devices of FIG. 2.

FIG. 3 is a diagram of example components of a device 300. Device 300 may correspond to transaction device 210, verification platform 220, and/or computing resource 224. In some implementations, transaction device 210, verification platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and/or a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random-access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
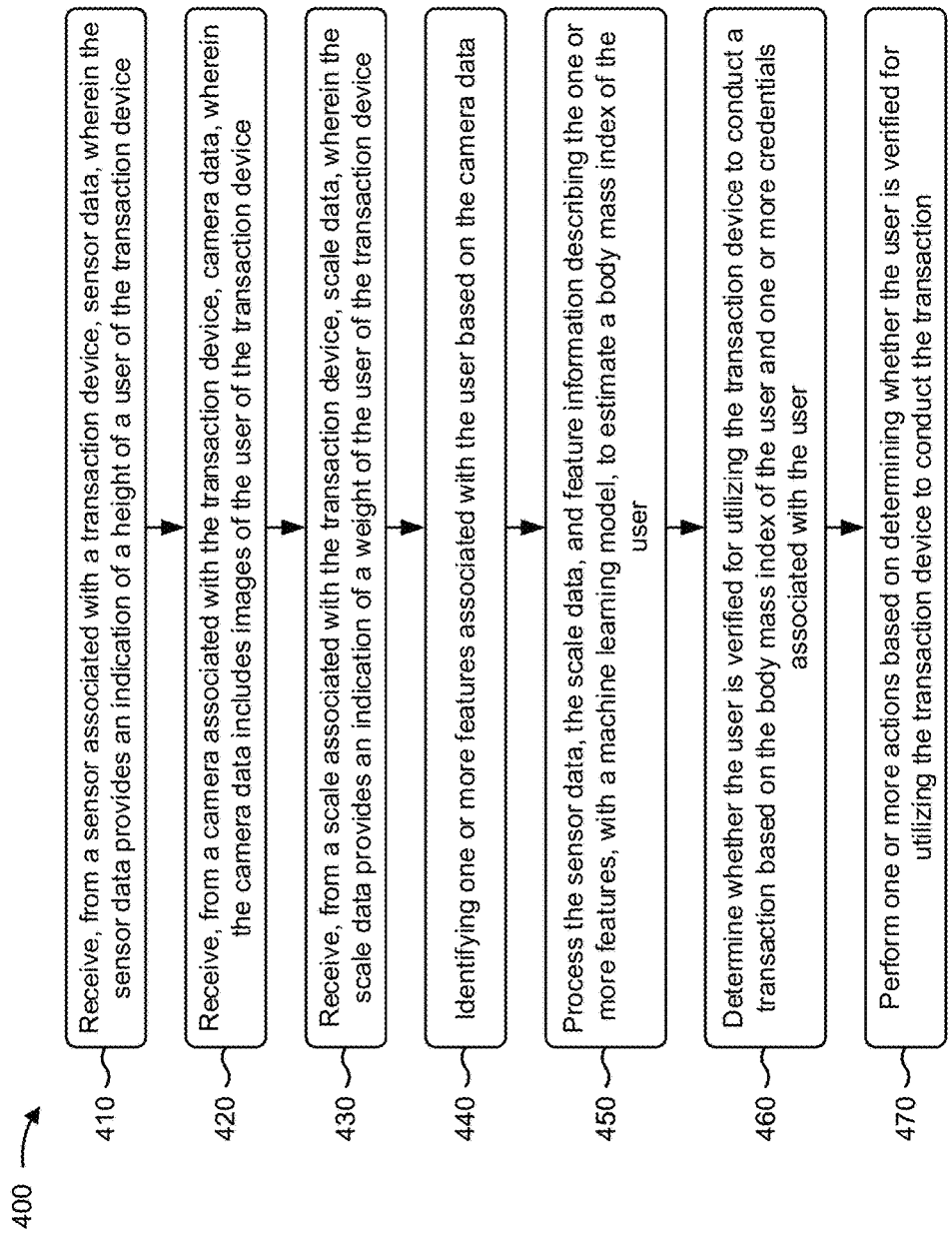

FIG. 4 is a flow chart of an example process 400 for determining a body mass index of a user of a transaction device and verifying the user for utilization of the transaction device based on the body mass index. In some implementations, one or more process blocks of FIG. 4 may be performed by a verification platform (e.g., verification platform 220). In some implementations, one or more process blocks of FIG. 4 may be performed by another device or a group of devices separate from or including the verification platform, such as a transaction device (e.g., transaction device 210).

As shown in FIG. 4, process 400 may include receiving, from a sensor associated with a transaction device, sensor data, wherein the sensor data provides an indication of a height of a user of the transaction device (block 410). For example, the verification platform (e.g., using computing resource 224, processor 320, communication interface 370, and/or the like) may receive, from a sensor associated with a transaction device, sensor data, as described above in connection with FIGS. 1A-2. In some implementations, the sensor data may provide an indication of a height of a user of the transaction device.

As further shown in FIG. 4, process 400 may include receiving, from a camera associated with the transaction device, camera data, wherein the camera data includes images of the user of the transaction device (block 420). For example, the verification platform (e.g., using computing resource 224, processor 320, memory 330, communication interface 370, and/or the like) may receive, from a camera associated with the transaction device, camera data, as described above in connection with FIGS. 1A-2. In some implementations, the camera data may include images of the user of the transaction device.

As further shown in FIG. 4, process 400 may include receiving, from a scale associated with the transaction device, scale data, wherein the scale data provides an indication of a weight of the user of the transaction device (block 430). For example, the verification platform (e.g., using computing resource 224, processor 320, storage component 340, communication interface 370, and/or the like) may receive, from a scale associated with the transaction device, scale data, as described above in connection with FIGS. 1A-2. In some implementations, the scale data may provide an indication of a weight of the user of the transaction device.

As further shown in FIG. 4, process 400 may include identifying one or more features associated with the user based on the camera data (block 440). For example, the verification platform (e.g., using computing resource 224, processor 320, memory 330, and/or the like) may identify one or more features associated with the user based on the camera data, as described above in connection with FIGS. 1A-2.

As further shown in FIG. 4, process 400 may process the sensor data, the scale data, and feature information describing the one or more features, with a machine learning model, to estimate a body mass index of the user (block 450). For example, the verification platform (e.g., using computing resource 224, processor 320, storage component 340, and/or the like) may process the sensor data, the scale data, and feature information describing the one or more features, with a machine learning model, to estimate a body mass index of the user, as described above in connection with FIGS. 1A-2.

As further shown in FIG. 4, process 400 may include determining whether the user is verified for utilizing the transaction device to conduct a transaction based on the body mass index of the user and one or more credentials associated with the user (block 460). For example, the verification platform (e.g., using computing resource 224, processor 320, memory 330, and/or the like) may determine whether the user is verified for utilizing the transaction device to conduct a transaction based on the body mass index of the user and one or more credentials associated with the user, as described above in connection with FIGS. 1A-2.

As further shown in FIG. 4, process 400 may include performing one or more actions based on determining whether the user is verified for utilizing the transaction device to conduct the transaction (block 470). For example, the verification platform (e.g., using computing resource 224, processor 320, memory 330, communication interface 370, and/or the like) may perform one or more actions based on determining whether the user is verified for utilizing the transaction device to conduct the transaction, as described above in connection with FIGS. 1A-2.

Process 400 may include additional implementations, such as any single implementation or any combination of implementations described below and/or described with regard to any other process described herein.

In some implementations, the one or more credentials associated with the user may include the height of the user, the weight of the user, a personal identification number (PIN) associated with the user, an account number associated with the user, and/or a telephone number associated with the user. In some implementations, when performing the one or more actions, the verification platform may provide, to the transaction device, information describing the body mass index of the user and information describing whether the user is verified to utilize the transaction device to conduct the transaction.

In some implementations, when performing the one or more actions, the verification platform may associate the body mass index of the user with a profile of the user, may cause the transaction device to request an additional credential from the user, may cause the transaction device to request that the user confirm the body mass index, may cause the transaction device to request that the user provide an estimated weight of clothing worn by the user, and/or may cause the transaction device to request that the user remove an article of clothing.

In some implementations, when performing the one or more actions, the verification platform may cause the transaction device to request that the user provide an actual height and/or weight of the user, may enable or prevent the transaction to be conducted with the transaction device, and/or may cause one or more of the sensor, the camera, or the scale to be recalibrated.

In some implementations, the camera data may indicate that the user is wearing particular clothing, and the verification platform may identify the particular clothing worn by the user, may estimate a weight of the particular clothing based on identifying the particular clothing, and may subtract the estimated weight from the weight of the user prior to calculating the body mass index of the user.

In some implementations, the camera data may indicate that the user is wearing particular type of shoes, and the verification platform may identify the particular shoes worn by the user, may determine a weight of the particular shoes based on identifying the particular shoes, may determine a height of the particular shoes based on identifying the particular shoes, may subtract the weight of the particular shoes from the weight of the user prior to calculating the body mass index of the user, and may subtract the height of the particular shoes from the height of the user prior to calculating the body mass index of the user.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
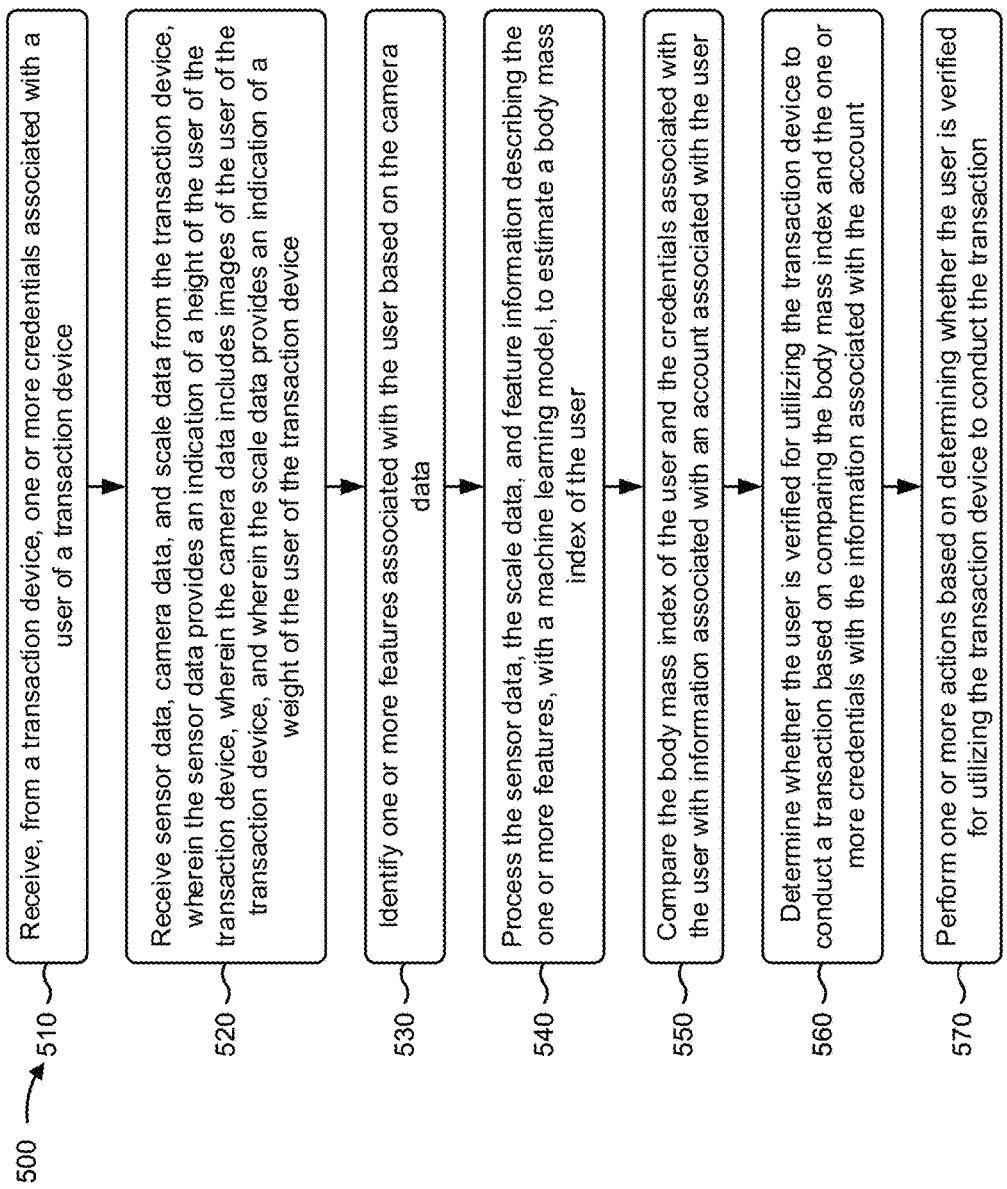

FIG. 5 is a flow chart of an example process 500 for determining a body mass index of a user of a transaction device and verifying the user for utilization of the transaction device based on the body mass index. In some implementations, one or more process blocks of FIG. 5 may be performed by a verification platform (e.g., verification platform 220). In some implementations, one or more process blocks of FIG. 5 may be performed by another device or a group of devices separate from or including the verification platform, such as a transaction device (e.g., transaction device 210).

As shown in FIG. 5, process 500 may include receiving, from a transaction device, one or more credentials associated with a user of a transaction device (block 510). For example, the verification platform (e.g., using computing resource 224, processor 320, communication interface 370, and/or the like) may receive, from a transaction device, one or more credentials associated with a user of a transaction device, as described above in connection with FIGS. 1A-2.

As further shown in FIG. 5, process 500 may include receiving sensor data, camera data, and scale data from the transaction device, wherein the sensor data provides an indication of a height of the user of the transaction device, wherein the camera data includes images of the user of the transaction device, and wherein the scale data provides an indication of a weight of the user of the transaction device (block 520). For example, the verification platform (e.g., using computing resource 224, processor 320, communication interface 370, and/or the like) may receive sensor data, camera data, and scale data from the transaction device, as described above in connection with FIGS. 1A-2. In some implementations, the sensor data may provide an indication of a height of the user of the transaction device. In some implementations, the camera data may include images of the user of the transaction device. In some implementations, the scale data may provide an indication of a weight of the user of the transaction device.

As further shown in FIG. 5, process 500 may include identifying one or more features associated with the user based on the camera data (block 530). For example, the verification platform (e.g., using computing resource 224, processor 320, memory 330, and/or the like) may identify one or more features associated with the user based on the camera data, as described above in connection with FIGS. 1A-2.

As further shown in FIG. 5, process 500 may include processing the sensor data, the scale data, and feature information describing the one or more features, with a machine learning model, to estimate a body mass index of the user (block 540). For example, the verification platform (e.g., using computing resource 224, processor 320, storage component 340, and/or the like) may process the sensor data, the scale data, and feature information describing the one or more features, with a machine learning model, to estimate a body mass index of the user, as described above in connection with FIGS. 1A-2.

As further shown in FIG. 5, process 500 may include comparing the body mass index of the user and the one or more credentials associated with the user with information associated with an account associated with the user (block 550). For example, the verification platform (e.g., using computing resource 224, processor 320, memory 330, and/or the like) may compare the body mass index of the user and the one or more credentials associated with the user with information associated with an account associated with the user, as described above in connection with FIGS. 1A-2.

As further shown in FIG. 5, process 500 may include determining whether the user is verified for utilizing the transaction device to conduct a transaction based on comparing the body mass index and the one or more credentials with the information associated with the account (block 560). For example, the verification platform (e.g., using computing resource 224, processor 320, storage component 340, and/or the like) may determine whether the user is verified for utilizing the transaction device to conduct a transaction based on comparing the body mass index and the one or more credentials with the information associated with the account, as described above in connection with FIGS. 1A-2.

As further shown in FIG. 5, process 500 may include performing one or more actions based on determining whether the user is verified for utilizing the transaction device to conduct the transaction (block 570). For example, the verification platform (e.g., using computing resource 224, processor 320, memory 330, communication interface 370, and/or the like) may perform one or more actions based on determining whether the user is verified for utilizing the transaction device to conduct the transaction, as described above in connection with FIGS. 1A-2.

Process 500 may include additional implementations, such as any single implementation or any combination of implementations described below and/or described with regard to any other process described herein.

In some implementations, the sensor data may be provided by a sensor associated with the transaction device, where the sensor includes one or more of a laser sensor or an ultrasound sensor; the camera data may be provided by a camera associated with the transaction device; and the scale data may be provided by a scale associated with the transaction device. In some implementations, the verification platform may provide, to the transaction device, information describing the body mass index of the user and information describing whether the user is verified to utilize the transaction device to conduct the transaction.

In some implementations, when performing the one or more actions, the verification platform may receive additional sensor data, additional camera data, and/or additional scale data from the transaction device when the user is not verified for utilizing the transaction device to conduct the transaction based on the body mass index; may identify one or more additional features associated with the user based on the additional camera data; and may process the additional sensor data, the additional scale data, and additional feature information describing the one or more additional features, with the machine learning model, to estimate another body mass index of the user.

In some implementations, when performing the one or more actions, the verification platform may cause the transaction device to request that the user provide an actual height and/or weight of the user; may enable or prevent execution of the transaction with the transaction device; and/or may cause one or more of a sensor, a camera, or a scale, associated with the transaction device, to be recalibrated. In some implementations, the verification platform may identify a width of the user based on the camera data, may estimate a weight of clothing worn by the user based on the width of the user, and may subtract the estimated weight from the weight of the user prior to calculating the body mass index of the user.

In some implementations, when performing the one or more actions, the verification platform may generate an alert when the user is not verified to utilize the transaction device to conduct the transaction, may decline the transaction when the user is not verified to utilize the transaction device to conduct the transaction, and/or may limit an amount of money dispensed by the transaction device when the user is not verified to utilize the transaction device to conduct the transaction.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

FIG. 6 is a flow chart of an example process 600 for determining a body mass index of a user of a transaction device and verifying the user for utilization of the transaction device based on the body mass index. In some implementations, one or more process blocks of FIG. 6 may be performed by a verification platform (e.g., verification platform 220). In some implementations, one or more process blocks of FIG. 6 may be performed by another device or a group of devices separate from or including the verification platform, such as a transaction device (e.g., transaction device 210).

As shown in FIG. 6, process 600 may include receiving, from a transaction device, sensor data, camera data, and scale data, wherein the sensor data provides an indication of a height of a user of the transaction device, wherein the camera data includes images of the user of the transaction device, and wherein the scale data provides an indication of a weight of the user of the transaction device (block 610). For example, the verification platform (e.g., using computing resource 224, processor 320, communication interface 370, and/or the like) may receive, from a transaction device, sensor data, camera data, and scale data, as described above in connection with FIGS. 1A-2. In some implementations, the sensor data may provide an indication of a height of a user of the transaction device. In some implementations, the camera data may include images of the user of the transaction device. In some implementations, the scale data may provide an indication of a weight of the user of the transaction device.

As further shown in FIG. 6, process 600 may include identifying one or more features associated with the user based on the camera data (block 620). For example, the verification platform (e.g., using computing resource 224, processor 320, storage component 340, and/or the like) may identify one or more features associated with the user based on the camera data, as described above in connection with FIGS. 1A-2.

As further shown in FIG. 6, process 600 may include adjusting the height of the user and/or the weight of the user, based on the one or more features associated with the user, to generate an adjusted height of the user and/or an adjusted weight of the user (block 630). For example, the verification platform (e.g., using computing resource 224, processor 320, memory 330, and/or the like) may adjust the height of the user and/or the weight of the user, based on the one or more features associated with the user, to generate an adjusted height of the user and/or an adjusted weight of the user, as described above in connection with FIGS. 1A-2.

As further shown in FIG. 6, process 600 may include processing the adjusted height and/or the adjusted weight, with a machine learning model, to estimate a body mass index of the user (block 640). For example, the verification platform (e.g., using computing resource 224, processor 320, storage component 340, and/or the like) may process the adjusted height and/or the adjusted weight, with a machine learning model, to estimate a body mass index of the user, as described above in connection with FIGS. 1A-2.

As further shown in FIG. 6, process 600 may include determining whether the user is verified for utilizing the transaction device to conduct a transaction based on the body mass index of the user and one or more credentials associated with the user (block 650). For example, the verification platform (e.g., using computing resource 224, processor 320, memory 330, and/or the like) may determine whether the user is verified for utilizing the transaction device to conduct a transaction based on the body mass index of the user and one or more credentials associated with the user, as described above in connection with FIGS. 1A-2.

As further shown in FIG. 6, process 600 may include performing one or more actions based on determining whether the user is verified for utilizing the transaction device to conduct the transaction (block 660). For example, the verification platform (e.g., using computing resource 224, processor 320, storage component 340, communication interface 370, and/or the like) may perform one or more actions based on determining whether the user is verified for utilizing the transaction device to conduct the transaction, as described above in connection with FIGS. 1A-2.

Process 600 may include additional implementations, such as any single implementation or any combination of implementations described below and/or described with regard to any other process described herein.

In some implementations, the verification platform may provide, to the transaction device, information describing the body mass index of the user, information describing previous body mass index measurements of the user, and information providing an indication of whether the user is verified for utilizing the transaction device to conduct the transaction.

In some implementations, when performing the one or more actions, the verification platform may provide, to the transaction device, information describing one or more recommended exercises for the user; may provide, to the transaction device, information describing one or more foods for the user to eat; and/or may provide, to the transaction device, information describing how the body mass index of the user compares with other users.

In some implementations, when performing the one or more actions, the verification platform may cause the transaction device to request that the user provide an actual height and/or weight of the user, may enable or prevent a transaction to be conducted with the transaction device, and/or may cause one or more of the sensor, the camera, or the scale to be recalibrated.

In some implementations, when performing the one or more actions, the verification platform may receive additional sensor data, additional camera data, and/or additional scale data from the transaction device when the user is not verified for utilizing the transaction device to conduct the transaction based on the body mass index; may identify one or more additional features associated with the user based on the additional camera data; and may process the additional sensor data, the additional scale data, and additional feature information describing the one or more additional features, with the machine learning model, to estimate another body mass index of the user.

In some implementations, the camera data may indicate that the user is holding a child or a bag, and the verification platform may estimate a weight of the child or the bag, and may subtract the estimated weight of the child or the bag from the weight of the user prior to calculating the body mass index of the user.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, and/or a combination of hardware and software.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
   receiving, by a device and from a sensor associated with a transaction device, sensor data, wherein the sensor data provides an indication of a height of a user of the transaction device;
   receiving, by the device and from a camera associated with the transaction device, camera data, wherein the camera data includes images of the user of the transaction device;
   receiving, by the device and from a scale associated with the transaction device, scale data, wherein the scale data provides an indication of a weight of the user of the transaction device;
   identifying, by the device, one or more features associated with the user based on the camera data;
   processing, by the device, the sensor data, the scale data, and feature information describing the one or more features, with a machine learning model, to estimate a body mass index of the user; determining, by the device, whether the user is verified for utilizing the transaction device to conduct a transaction, based on the body mass index of the user and one or more credentials associated with the user; and
   performing, by the device, one or more actions based on determining whether the user is verified for utilizing the transaction device to conduct the transaction,
      wherein performing the one or more actions includes one or more of:
         associating the body mass index of the user with a profile of the user;
         causing the transaction device to request an additional credential from the user;
         causing the transaction device to request that the user confirm the body mass index;
         causing the transaction device to request that the user provide an estimated weight of clothing worn by the user;
         causing the transaction device to request that the user remove an article of clothing;
         causing the transaction device to request that the user provide an actual height and/or weight of the user;
         enabling or preventing the transaction to be conducted with the transaction device; or
         causing one or more of the sensor, the camera, or the scale to be recalibrated.

2. The method of claim 1, wherein the one or more credentials associated with the user includes one or more of:
   the height of the user,
   the weight of the user, a personal identification number (PIN) associated with the user,
an account number associated with the user, or
a telephone number associated with the user.

3. The method of claim 1, wherein performing the one or more actions further includes:
providing, to the transaction device, information describing the body mass index of the user and information describing whether the user is verified to utilize the transaction device to conduct the transaction.

4. The method of claim 1, wherein the camera data indicates that the user is wearing particular clothing and the method further comprises:
identifying the particular clothing worn by the user;
estimating a weight of the particular clothing based on identifying the particular clothing; and
subtracting the estimated weight from the weight of the user prior to calculating the body mass index of the user.

5. The method of claim 1, wherein the camera data indicates that the user is wearing particular shoes and the method further comprises:
identifying the particular shoes worn by the user;
determining a weight of the particular shoes based on identifying the particular shoes;
determining a height of the particular shoes based on identifying the particular shoes;
subtracting the weight of the particular shoes from the weight of the user prior to calculating the body mass index of the user; and
subtracting the height of the particular shoes from the height of the user prior to calculating the body mass index of the user.

6. A device, comprising:
one or more memories; and
one or more processors, communicatively coupled to the one or more memories, configured to:
receive, from a transaction device, one or more credentials associated with a user of a transaction device;
receive sensor data, camera data, and scale data from the transaction device,
wherein the sensor data provides an indication of a height of the user of the transaction device,
wherein the camera data includes images of the user of the transaction device, and
wherein the scale data provides an indication of a weight of the user of the transaction device;
identify one or more features associated with the user based on the camera data;
process the sensor data, the scale data, and feature information describing the one or more features, with a machine learning model, to estimate a body mass index of the user;
compare the body mass index of the user and the one or more credentials associated with the user with information associated with an account associated with the user;
determine whether the user is verified for utilizing the transaction device to conduct a transaction based on comparing the body mass index and the one or more credentials with the information associated with the account; and
perform one or more actions based on determining whether the user is verified for utilizing the transaction device to conduct the transaction,
wherein, when performing the one or more actions, the one or more processors are configured to one or more of:
cause the transaction device to request that the user provide an actual height and/or weight of the user;
enable or prevent the transaction to be conducted with the transaction device;
cause one or more of a sensor, a camera, or a scale, associated with the transaction device, to be recalibrated;
generate an alert when the user is not verified to utilize the transaction device to conduct the transaction;
decline the transaction when the user is not verified to utilize the transaction device to conduct the transaction; or
limit an amount of money dispensed by the transaction device when the user is not verified to utilize the transaction device to conduct the transaction.

7. The device of claim 6, wherein:
the sensor data is provided by a sensor associated with the transaction device, wherein the sensor includes one or more of a laser sensor or an ultrasound sensor;
the camera data is provided by a camera associated with the transaction device; and
the scale data is provided by a scale associated with the transaction device.

8. The device of claim 6, wherein the one or more processors are further configured to:
provide, to the transaction device, information describing the body mass index of the user and information describing whether the user is verified to utilize the transaction device to conduct the transaction.

9. The device of claim 6, wherein, when performing the one or more actions, the one or more processors are further configured to:
receive additional sensor data, additional camera data, and additional scale data from the transaction device when the user is not verified for utilizing the transaction device to conduct the transaction based on the body mass index;
identify one or more additional features associated with the user based on the additional camera data; and
process the additional sensor data, the additional scale data, and additional feature information describing the one or more additional features, with the machine learning model, to estimate another body mass index of the user.

10. The device of claim 6, wherein the one or more processors are further configured to:
identify a width of the user based on the camera data;
estimate a weight of clothing worn by the user based on the width of the user; and
subtract the estimated weight from the weight of the user prior to calculating the body mass index of the user.

11. A non-transitory computer-readable medium storing instructions, the instructions comprising:
one or more instructions that, when executed by one or more processors of a device, cause the one or more processors to:
receive, from a transaction device, sensor data, camera data, and scale data,
wherein the sensor data provides an indication of a height of a user of the transaction device,
wherein the camera data includes images of the user of the transaction device, and
wherein the scale data provides an indication of a weight of the user of the transaction device;

identify one or more features associated with the user based on the camera data;
adjust the height of the user and/or the weight of the user, based on the one or more features associated with the user, to generate an adjusted height of the user and/or an adjusted weight of the user;
process the adjusted height and/or the adjusted weight, with a machine learning model, to estimate a body mass index of the user;
determine whether the user is verified for utilizing the transaction device to conduct a transaction, based on the body mass index of the user and one or more credentials associated with the user; and
perform one or more actions based on determining whether the user is verified for utilizing the transaction device to conduct the transaction,
wherein the one or more instructions, that cause the one or more processors to perform the one or more actions, cause the one or more processors to one or more of:
provide, to the transaction device, information describing one or more recommended exercises for the user;
provide, to the transaction device, information describing one or more foods for the user to eat;
provide, to the transaction device, information describing how the body mass index of the user compares with other users;
cause the transaction device to request that the user provide an actual height and/or weight of the user; or
enable or prevent a transaction to be conducted with the transaction device.

12. The non-transitory computer-readable medium of claim 11, wherein the instructions further comprise:
one or more instructions that, when executed by the one or more processors, cause the one or more processors to:
provide, to the transaction device:
information describing the body mass index of the user,
information describing previous body mass index measurements of the user, and
information providing an indication of whether the user is verified for utilizing the transaction device to conduct the transaction.

13. The non-transitory computer-readable medium of claim 11, wherein the one or more instructions, that cause the one or more processors to perform the one or more actions, further cause the one or more processors to one or more of:
receive additional sensor data, additional camera data, and additional scale data from the transaction device when the user is not verified for utilizing the transaction device to conduct the transaction based on the body mass index;
identify one or more additional features associated with the user based on the additional camera data; and
process the additional sensor data, the additional scale data, and additional feature information describing the one or more additional features, with the machine learning model, to estimate another body mass index of the user.

14. The non-transitory computer-readable medium of claim 11, wherein the camera data indicates that the user is holding a child or a bag and the instructions further comprise:
one or more instructions that, when executed by the one or more processors, cause the one or more processors to:
estimate a weight of the child or the bag; and
subtract the estimated weight of the child or the bag from the weight of the user prior to calculating the body mass index of the user.

15. The method of claim 1, wherein the transaction device includes the sensor, the camera, and the scale.

16. The method of claim 1, wherein the transaction device is an electronic communication device that enables the user to perform one or more financial transactions.

17. The device of claim 6, wherein the transaction device includes one or more of the sensor, the camera, or the scale.

18. The device of claim 6, wherein the transaction device is an electronic communication device that enables the user to perform one or more financial transactions.

19. The non-transitory computer-readable medium of claim 11,
wherein:
the sensor data is provided by a sensor associated with the transaction device,
the camera data is provided by a camera associated with the transaction device; and
the scale data is provided by a scale associated with the transaction device, and
wherein the transaction device includes one or more of the sensor, the camera, or the scale.

20. The non-transitory computer-readable medium of claim 11, wherein the transaction device is an electronic communication device that enables the user to perform one or more financial transactions.

* * * * *